(12) United States Patent
Kumagai et al.

(10) Patent No.: US 8,338,442 B2
(45) Date of Patent: Dec. 25, 2012

(54) REMEDIES FOR PSYCHONEUROSIS

(75) Inventors: Hiroo Kumagai, Tokyo (JP); Jun Utsumi, Tokyo (JP)

(73) Assignee: Toray Industries, Inc. (JP)

( * ) Notice: Subject to any disclaimer, the term of this patent is extended or adjusted under 35 U.S.C. 154(b) by 945 days.

(21) Appl. No.: 10/473,541

(22) PCT Filed: Mar. 29, 2002

(86) PCT No.: PCT/JP02/03156
§ 371 (c)(1),
(2), (4) Date: Sep. 29, 2003

(87) PCT Pub. No.: WO02/078744
PCT Pub. Date: Oct. 10, 2002

(65) Prior Publication Data
US 2004/0116456 A1 Jun. 17, 2004

(30) Foreign Application Priority Data
Mar. 30, 2001 (JP) .............................. 2001-100797

(51) Int. Cl.
*A61K 31/44* (2006.01)
(52) U.S. Cl. ..................... 514/279; 514/284
(58) Field of Classification Search .................. 514/284, 514/279, 842
See application file for complete search history.

(56) References Cited

U.S. PATENT DOCUMENTS

| | | | | |
|---|---|---|---|---|
| 6,114,326 A * | 9/2000 | Schueler | ....................... | 514/220 |
| 6,277,859 B1 * | 8/2001 | Nagase et al. | ................ | 514/282 |

FOREIGN PATENT DOCUMENTS

| | | |
|---|---|---|
| CA | 2106072 A1 | 9/1992 |
| CN | 1214634 A | 4/1999 |
| EP | 0 260 041 A1 | 3/1888 |
| EP | 0 126 612 A1 | 11/1984 |
| EP | 0 232 612 A1 | 8/1987 |
| EP | 0 275 696 A1 | 7/1988 |
| EP | 0 657 443 A1 | 6/1995 |
| EP | 0 974 363 A1 | 1/2000 |
| WO | 98/23290 A1 | 6/1998 |
| WO | 99 48484 A2 | 9/1999 |
| WO | 00 25821 A1 | 5/2000 |
| WO | 01 13903 A2 | 3/2001 |

OTHER PUBLICATIONS

Hening W.A. et al. (1986) Dyskinesias while awake and periodic movements in sleep in restless legs syndrome: Treatment with opiods. Neurology 36: 1363-1366.*
Victor Collado-Seidel et al., "Aetiology and Treatment of Restless Legs Syndrome", CNS Drugs Jul. 12, 1999, pp. 9-20.
Wayne Henin,MD, PhD., et al., "The Treatment of Restless Legs Syndrome and Periodic Limb Movement Disorder", Sleep, vol. 22, Nov. 7, 1999, pp. 970-999.

Fraser B. Ross et al., "The intrinsic antinociceptive effects of oxycodone appear to be κ-opioid receptor mediated," Pain, vol. 73, 1997, pp. 151-157.
Saito, T. et al., "Erinacine E as a Kappa Opioid Receptor Agonist and Its New Analogs from a Basidiomycete, Hericiam Ramosum," *J. Antibiot.*, 1998, vol. 51, No. 5, pp. 983-990 (Abstract—1 sheet).
Giuliani, S. et al., "Role of Kappa Opioid Receptors in Modulating Cholinergic Twitches in the Circular Muscle of Guinea-Pig Colon," *Br. J. Pharmacol.*, Nov. 1996, vol. 119, No. 5, pp. 985-989 (Abstract—1 sheet).
Szmuszkovicz, J. et al., "Benzeneacetamide Amines: Structurally Novel Non-Mµ Opioids," *J. Med. Chem.*, 1982, vol. 25, No. 10, pp. 1125-1126 (Abstract—1 sheet).
Halfpenny, P.R. et al., "Highly Selective Kappa-Opioid Analgesics 3. Synthesis and Structure-Activity Relationships of Novel N-(2-(1-pyrrolidinyl)-4-or 5-substituted-cyclohexyljaryiacetamide Derivatives," *J. Med. Chem.*, Jan. 1990, vol. 33, No. 1, pp. 286-291 (Abstract—1 sheet).
Vecchietti, V. et al., "(2S)-1-(arylacetyl)-2-(aminomethyl)piperidine Derivatives: Novel, Highly Selective Kappa Opioid Analgesics," *J. Med. Chem.*, Jan. 1991, vol. 34, No. 1, pp.397-403 (Abstract—1 sheet).
Scopes, D.J. et al., "New Kappa-Receptor Agonists Based upon a 2 ((alkylamino)methyl)piperidine Nucleus, " J. Med. Chem., Feb. 1992, vol. 35, No. 3, pp. 490-501 (Abstract—1 sheet).
Naylor, A. et al., "A Potent New Class of Kappa-Receptor Agonist: 4 Substituted 1-(arylacetyl)-2-[(dialkylamino)methyl]piperidines," *J. Med. Chem.*, Jul. 1993, vol. 36, No. 15, pp. 2075-2083 (Abstract—1 sheet).
Barlow, J.J. et al., "Structure/Activity Studies Related to 2-(3,4-Dichlorophenyl)-*N*-methyl-N-(2-(1-pyrrolidinyl)-1-substitutedethyl)acetamides: a Novel Series of Potent and Selective κ-Opioid Agonists, " *J. Med. Chem.*, Nov. 1991, vol. 34, No. 11, pp. 3149-3158 (1st page only).
*Restless Legs Syndrome Foundation, Inc.*[Online] April 2001, pp. 1-8, 18-23, Retrieved from the Internet:<URL:http://www.rsl.org/pdf/med_bulletin/2001MB.pdf> [retrieved on May 27, 2002] (Title/Source—1 sheet).
Walters A.S. et al., "Successful Treatment of the Idiopathic Restless Legs Syndrome in a Randomized Double-Blind Trial of Oxycodone Versus Placebo, " *Sleep*, 1993, vol. 16, No. 4, pp. 327-332.
Chesson, A.L. Jr. et al., "Practice Parameters for the Treatment of Restless Legs Syndrome and Periodic Limb Movement Disorder. An American Academy of Sleep Medicine Report. Standards of Practice committee of the American Academy of Sleep Medicine, " *Sleep*, Nov. 1999, vol. 22, No. 7, pp. 961-968 (Abstract—1 sheet).
Horiguchi, "Current Insights In Neurological Science, " Science, 1997, vol. 4, No. 2, p. 8 (Parial English Translation—1 sheet).
"Japan Drugs," edited by Japan Drugs committee, *Medical Review Co., Ltd.*, 1994, pp. 1363-1365 (Partial English Translation—1 sheet).

* cited by examiner

*Primary Examiner* — Sreeni Padmanabhan
*Assistant Examiner* — Renee Claytor
(74) *Attorney, Agent, or Firm* — DLA Piper LLP (US)

(57) ABSTRACT

A therapeutic drug for psychoneurotic disorders, which is useful for therapies of psychoneurotic disorders, especially restless legs syndrome is disclosed. The therapeutic drug for psychoneurotic disorders according to the present invention comprises as an effective ingredient an opioid κ receptor agonist compound (excluding pentazocine) such as (−)-17-(cyclopropylmethyl)-3,14β-dihydroxy-4,5α-epoxy-6β[N-methyl-trans-3-(3-furyl)acrylamide]morphinan hydrochloric acid salt.

6 Claims, No Drawings

REMEDIES FOR PSYCHONEUROSIS

TECHNICAL FIELD

This disclosure relates to a therapeutic drug for psychoneurotic disorders. The therapeutic drug for psychoneurotic disorders are useful for therapies of psychoneurotic disorders such as restless legs syndrome (hereinafter also referred to as "RLS").

BACKGROUND ART

RLS is a nervous system disorder, which is thought to be one of the peripheral neuropathies, which gives very uncomfortable abnormal sensation that is a strong itchy sensation on the lower limbs at rest or when falling asleep. Although in some cases, the itchy sensation is also felt on the upper limbs or the trunk, the disorder is characterized by the strong abnormal sensation on the lower limbs as expressed in its name. If RLS is once started, it is impossible to keep the legs still and the patient chafes the soles or moves the legs in order to try to alleviate the symptom even in the slightest degree. In severe cases, the patient cannot keep still on the bed, so that the patient stands up and walks around. Such uncomfortable sensation on the lower limbs cannot be appreciated by those who have not experienced it. According to the complaints by patients themselves, the sensation is often expresses as "itchy" or "as if ants are creeping" (formication). Since RLS often occurs in the night when the patient is falling asleep, the patients cannot keep still, and the falling asleep or the falling asleep in the second time after intermediate awakening is disturbed, so that the patients suffer from severe insomnia. Due to the chronic shortage of sleep, the patients are tired and may suffer from strong fret. Reported pathological states which cause RLS include anemia (iron deficiency anemia), renal failure, uremia, gastrectomy, pregnancy, metabolic diseases (diabetes, porphyria, gout, amyloidosis and the like), infectious diseases (tuberculosis, pneumonia, hepatitis, poliomyelitis and the like), venous thrombosis in lower limbs, drugs (promethazine, prochlorperazine, barbiturates and the like), coldness and psychic factors (Zenji SHIOZAWA et al., Journal of New Remedies & Clinics, Vol. 49, 218-255, 2000).

As the cause of RLS, the publication (NIH Publication No. 00-3788, March 2000) by U.S. National Institute of Health (NIH) suggests secondary onset accompanying the above-mentioned pathological states and familial genetic factors as well as drugs such as tricyclic antidepressants, selective serotonin resorption inhibitors (SSRIs), lithium, dopamine antagonists and caffeine.

Although no survey has been carried out, which precisely measures prevalence of RLS, the prevalence of RLS is estimated to be 2 to 15% in the U.S. based on the total population (NIH Publication No. 00-3788) or 3 to 8% (publication in Japanese by the U.S. RLS Foundation, 1999), 1 to 5% in Europe and 1 to 3% in Japan (Yuichi INOUE et al., Journal of New Remedies & Clinics, Vol. 49, 244-255, 2000). When classified according to the pathological states, the prevalence in the patients suffering from renal failure is extremely high, and is estimated to be about 50% in both the U.S. and Japan (Isao EGAWA et al., New Remedies & Clinics, Vol. 49, 230-235, 2000). RLS is one of the major causes which impair quality of life of the patients. Those which are thought to be symptoms or disorders similar to RLS include periodic limb movements (PLM), myoclonic syndrome, contractions and painful contraction.

Since the cause of RLS has not been well clarified, radical therapy thereof has not been established. In the U.S., there is no drug which was approved by FDA for use against RLS. Although various chemotherapies are now being tried, including those using dopamine agonist, opioid (opioid μ receptor agonist), benzodiazepine, anticonvulsants and the like, they have problems in that the effectiveness is insufficient, sleepiness is carried over until the morning or the effectiveness is reduced with continuous use, so that none of them has been established as a therapeutic method. Opioid drugs which have been applied to RLS include opioid μ receptor agonists such as codeine, hydrocodeine, oxycodone, propoxyphene, tramadol and methadone, and pentazocine which is an opioid μ and κ receptor agonist. However, all of them have insufficient effectivities and problems of side effects or dependency, so that medical satisfactions thereof are poor (NIH Publication No. 00-3788; publication in English by the U.S. RLS Foundation, 2000, Pentagin: U.S. Pat. No. 6,114,326).

In the U.S., RLS Research Foundation was founded. It enlightens the correct understanding of the disease and hints on the life, and supports the research for therapeutic methods.

Thus, in spite of the fact that RLS is very uncomfortable to the patients and decreases the quality of life, the cause thereof has not been clarified and effective therapeutic method has not been established. Thus, RLS is a big problem in medicine and development of more useful therapeutic method is strongly demanded.

It could therefore be advantageous to provide a therapeutic drug for psychoneurotic disorders, which is useful for the therapies of nervous diseases, especially restless legs syndrome.

SUMMARY

We provide a therapeutic drug for psychoneurotic disorders comprising an opioid κ receptor agonist compound (excluding pentazocine) as an effective ingredient. We also provide a use of an opioid κ receptor agonist compound (excluding pentazocine) for the production of a therapeutic drug for psychoneurotic disorders. We further provide a method of therapy for psychoneurotic disorders, comprising administering an effective amount of an opioid κ receptor agonist compound (excluding pentazocine).

DETAILED DESCRIPTION

The opioid κ receptor agonist compound includes compounds which exhibit affinities to κ receptor irrespective of chemical structural specificity. Those which are more selective to κ receptor than to μ and δ receptors are preferred. More particularly, preferred examples thereof include those represented by Formula (I):

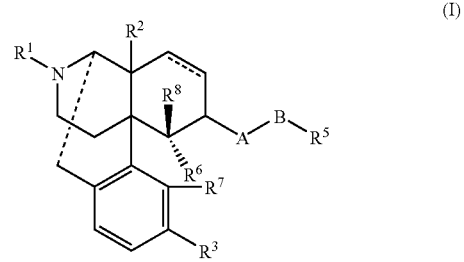

[wherein ═══ represents double bond or single bond; $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, $C_1$-$C_5$ furan-2-yl-alkyl or $C_1$-$C_5$ thiophene-2-yl-alkyl; $R^2$ represents hydrogen, hydroxy, nitro, $C_1$-$C_5$ alkanoyloxy, $C_1$-$C_5$ alkoxy, $C_1$-$C_5$ alkyl or $NR^9R^{10}$ wherein $R^9$ represents hydrogen or $C_1$-$C_5$ alkyl, and $R^{10}$ represents hydrogen, $C_1$-$C_5$ alkyl or —C(=O)$R^{11}$— wherein $R^{11}$ represents hydrogen, phenyl or $C_1$-$C_5$ alkyl; $R^3$ represents hydrogen, hydroxy, $C_1$-$C_5$ alkanoyloxy or $C_1$-$C_5$ alkoxy; A represents —XC(=Y)—, —XC(=Y)Z—, —X— or —XSO$_2$— (wherein X, Y and Z independently represent $NR^4$, S or O; $R^4$ represents hydrogen, $C_1$-$C_5$ linear or branched alkyl or $C_6$-$C_{12}$ aryl, wherein $R^4$s may be the same or different); B represents valence bond, $C_1$-$C_{14}$ linear or branched alkylene (with the proviso that said alkylene may have at least one substituent selected from the group consisting of $C_1$-$C_5$ alkoxy, $C_1$-$C_5$ alkanoyloxy, hydroxy, fluorine, chlorine, bromine, iodine, amino, intro, cyano, trifluoromethyl and phenoxy, and that 1 to 3 methylene groups may be substituted by carbonyl group(s)), $C_2$-$C_{14}$ linear or branched acyclic unsaturated hydrocarbon containing 1 to 3 double bonds and/or triple bonds (with the proviso that said acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups may be substituted by carbonyl group(s)), or $C_1$-$C_{14}$ linear or branched saturated or unsaturated hydrocarbon containing 1 to 5 thioether bonds, ether bonds and/or amino bonds (with the proviso that hetero atom does not directly bind to A, and 1 to 3 methylene groups may be substituted by carbonyl group(s)); $R^5$ represents hydrogen or an organic group having one of the following skeletons:

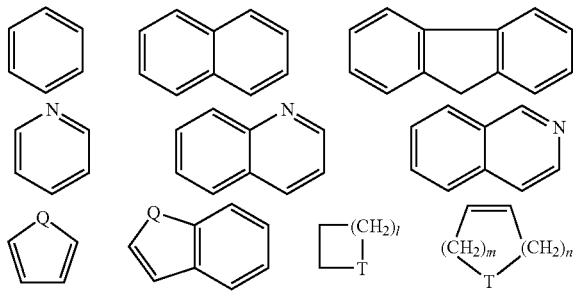

(wherein Q represents —NH—, —O— or —S—; T represents —CH$_2$—, —NH—, —S— or —O—; l represents an integer of 0 to 5; and m and n independently represent integers of not less than 0, the sum of m and n being not more than 5) (with the proviso that the skeletons may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, intro, cyano, isothiocyanato, trifluoromethyl, trifluoromethoxy and methylenedioxy);

$R^6$ represents hydrogen; $R^7$ represents hydrogen, hydroxy, $C_1$-$C_5$ alkoxy, $C_1$-$C_5$ alkanoyloxy, or $R^6$ and $R^7$ cooperatively represent —O—, —CH$_2$— or —S—; and $R^8$ represents hydrogen, $C_1$-$C_5$ alkyl or $C_1$-$C_5$ alkanoyl; said Formula (I) includes (+) isomer, (−) isomer and (±) isomer] and pharmaceutically acceptable acid addition salts thereof.

In the case of a group such as "alkyl" or "alkoxy", wherein there are linear and branched types, both linear and branched groups are included in the present specification unless otherwise specified. In the definition of $R^5$ in the above-described Formula (I), the term "an organic group having a skeleton" means a monovalent group formed by elimination of one hydrogen atom from the ring constituting the respective compound shown as the above-mentioned skeleton or the thus formed monovalent group having the above-mentioned substituent(s).

In the compounds represented by Formula (I), preferred examples of $R^1$ include $C_1$-$C_5$ alkyl, $C_4$-$C_7$ cycloalkylmethyl, $C_5$-$C_7$ cycloalkenylmethyl, $C_7$-$C_{13}$ phenylalkyl, $C_4$-$C_7$ alkenyl, allyl, $C_1$-$C_5$ furan-2-yl-alkyl and $C_1$-$C_5$ thiophene-2-yl-alkyl. Among these, methyl, ethyl, propyl, butyl, isobutyl, cyclopropylmethyl, allyl, benzyl, phenethyl, furan-2-yl-methyl and thiophene-2-yl-methyl are preferred.

Preferred examples of $R^2$ include hydrogen, hydroxy, nitro, acetoxy, methoxy, methyl, ethyl, propyl, amino, dimethylamino, acetylamino and benzoylamino. Among these, hydrogen, hydroxy, nitro, acetoxy, methoxy, methyl and dimethylamino, especially, hydrogen, hydroxy, acetoxy and methoxy, are preferred.

As $R^3$, hydrogen, hydroxy, acetoxy and methoxy are preferred, especially, hydroxy, acetoxy and methoxy are preferred.

Preferred concrete examples of A include —NR$^4$C(=O)—, —NR$^4$C(=S)—, —NR$^4$C(=O)O—, —NR$^4$C(=O)NR$^4$—, —NR$^4$C(=S)NR$^4$—, —NR$^4$C(=O)S—, —OC(=O)—, —OC(=O)O—, —SC(=O)—, —NR$^4$—, —O—, —NR$^4$SO$_2$— and —OSO$_2$—. Among these, —NR$^4$C(=O)—, —NR$^4$C(=S)—, —NR$^4$C(=O)O—, —NR$^4$C(=O)NR$^4$—, —NR$^4$C(=S)NR$^4$— and —NR$^4$SO$_2$— are preferred. As the $R^4$, hydrogen and $C_1$-$C_5$ linear or branched alkyl are preferred. Particularly, $C_1$-$C_5$ linear or branched alkyl, especially, methyl, ethyl, propyl, butyl and isobutyl are preferred. Among those mentioned above, —XC(=Y)— (wherein X represents NR$^4$, S or O; Y represents O; and R$^4$ represents hydrogen or $C_1$-$C_5$ alkyl), —XC(=Y)Z—, —X—, —XSO$_2$— (wherein X represents NR$^4$; Y represents O or S; Z represents NR$^4$ or O; and R$^4$ represents hydrogen or $C_1$-$C_5$ alkyl), —XC(=Y)— and —XC(=Y)Z— (wherein X represents NR$^4$, Y represents O, Z represents O and R$^4$ represents $C_1$-$C_5$ alkyl) are preferred. Especially, —XC(=Y)— (wherein X represents NR$^4$, Y represents O and R$^4$ represents $C_1$-$C_5$ alkyl) are preferred.

Preferred examples of B include —(CH$_2$)$_n$— (n=0-10), —(CH$_2$)$_n$—C(=O)— (n=1-4), —CH=CH—(CH$_2$)$_n$— (n=0-4), —C≡C—(CH$_2$)$_n$— (n=0-4), —CH$_2$—O—, —CH$_2$—S—, —(CH$_2$)$_2$—O—CH$_2$— and —CH=CH—CH=CH—(CH$_2$)$_n$— (n=0-4), especially —(CH$_2$)$_n$— (n=1-3), —CH=CH—(CH$_2$)$_n$— (n=0-4), —C≡C—(CH$_2$)$_n$— (n=0-4), —CH$_2$—O— and —CH$_2$—S—. Among these, $C_1$-$C_3$ linear alkylene, —CH=CH—, —C≡C—, —CH$_2$O— and —CH$_2$S—, especially, —CH=CH— and —C≡C—, are more preferred (needless to say, these preferred examples include those having the above-mentioned various substituents).

As the $R^5$, hydrogen and the organic groups having one of the following skeletons are preferred:

(wherein the definitions of Q, T, l, m and n are the same as described above), (with the proviso that the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, amino, nitro, cyano, isothiocyanato, trifluoromethyl, trifluoromethoxy and methylenedioxy).

Among the above-described $R^5$, preferred are hydrogen, phenyl, thienyl and furanyl (with the proviso that these organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, amino, nitro, cyano, isothiocyanato, trifluoromethyl, trifluoromethoxy and methylenedioxy).

More specific preferred examples include hydrogen, phenyl, 4-methylphenyl, 3-methylphenyl, 2-methylphenyl, 3,4-dimethylphenyl, 3,5-dimethylphenyl, 4-methoxyphenyl, 3-methoxyphenyl, 2-methoxyphenyl, 3,4-dimethoxyphenyl, 4-hydroxyphenyl, 3-hydroxyphenyl, 3,4-dihydroxyphenyl, 4-fluorophenyl, 3-fluorophenyl, 2-fluorophenyl, 3,4-difluorophenyl, perfluorophenyl, 4-chlorophenyl, 3-chlorophenyl, 2-chlorophenyl, 3,4-dichlorophenyl, 2,4-dichlorophenyl, 2,4,5-trichlorophenyl, 2,4,6-trichlorophenyl, 4-bromophenyl, 3-bromophenyl, 2-bromophenyl, 4-nitrophenyl, 3-nitrophenyl, 2-nitrophenyl, 4-aminophenyl, 3-aminophenyl, 2-aminophenyl, 4-trifluoromethylphenyl, 3-trifluoromethylphenyl, 2-trifluoromethylphenyl, 4-trifluoromethoxyphenyl, 3-trifluoromethoxyphenyl, 2-trifluoromethoxyphenyl, 3,4-methylenedioxyphenyl, 3-furanyl, 2-furanyl, 3-thienyl, 2-thienyl, cyclopentyl and cyclohexyl. Needless to say, however, $R^5$ is not restricted to these groups.

The opioid κ receptor agonist compounds represented by Formula (I) may be produced by the method described in Japanese Patent No. 2525552.

Preferred examples of opioid κ receptor agonist compound include the compounds represented by the following Formula (II):

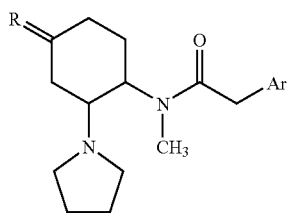

(II)

[wherein R represents two hydrogen atoms or —O—CH₂CH₂CH₂—; Ar represents

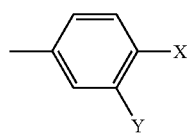

(wherein X and Y independently represent hydrogen or chlorine)

or

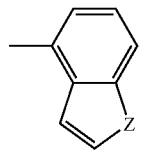

(wherein Z represents O or S);
said Formula (II) includes (+) isomer, (−) isomer and (±) isomer]
and pharmaceutically acceptable acid addition salts thereof.

Among the compounds represented by Formula (II), trans-2-(3,4-dichlorophenyl)-N-methyl-N-[2-(1-pyrrolidinyl)cyclohexyl]acetamide, trans-N-methyl-N-[2-(1-pyrrolidinyl)cyclohexyl]benzo[b]thiophene-4-acetamide, (5β,7β,8α)-3,4-dichloro-N-methyl-N-[7-(1-pyrrolidinyl)-1-oxaspiro[4,5]dec-8-yl]benzene acetamide, (5β,7β,8α)-N-methyl-N-[7-(1-pyrrolidinyl)-1-oxaspiro[4,5]dec-8-yl]benzo[b]furan-4-acetamide, and (5β,7β,8α)-N-methyl-N-[7-(1-pyrrolidinyl)-1-oxaspiro[4,5]dec-8-yl]benzene acetamide are preferred.

The opioid κ receptor agonist compounds represented by Formula (II) may be produced by the methods described in J. Szmuszkovicz et al., J. Med. Chem., 25, 1125 (1982); D. C. Horwell et al., U.S. Pat. No. 5,587,37 (1983); J. Szmuszkovicz et al., Eur. Patent Appl. EP126612 (1984); and P. R. Halfpenny, D. C. Horwell et al., J. Med. Chem., 33, 286 (1990).

Preferred examples of opioid κ receptor agonist compound also include the compounds represented by the following Formula (III):

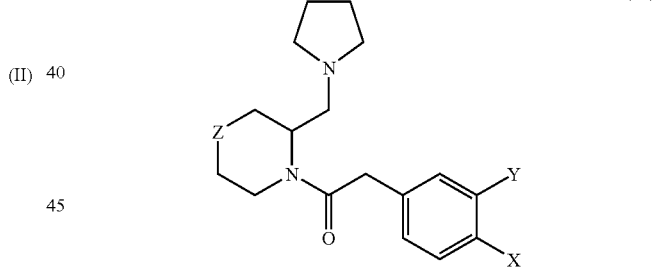

(III)

[wherein X represents hydrogen, chlorine or trifluoromethyl; Y represents hydrogen or chlorine; and Z represents —CH₂—, —OCH₂CH₂O— or =NCO₂CH₃; said Formula (III) includes (+) isomer, (−) isomer and (±) isomer]
and pharmaceutically acceptable acid addition salts thereof.

Among the compounds represented by Formula (III), methyl 4-[(3,4-dichlorophenyl)acetyl]-3-[(1-pyrrolidinyl)methyl]-1-piperazine carboxylate, 1-[(4-trifluoromethylphenyl)acetyl]-2-[(1-pyrrolidinyl)methyl]piperidine, 1-[(3,4-dichlorophenyl)acetyl]-2-[(1-pyrrolidinyl)methyl]piperidine and 1-[(3,4-dichlorophenyl)acetyl]-4,4-ethylenedioxy-2-[(1-pyrrolidinyl)methyl]piperidine are preferred.

The opioid κ receptor agonist compounds represented by Formula (III) may be produced by the methods described in A. Naylor et al., J. Med. Chem., 36, 2075 (1993); V. Vecchietti et al., J. Med. Chem., 34, 397 (1991), ibid. Eur. Patent Appl. EP232,612 (1987); EP260,041 (1988); EP275,696 (1988); and D. I. C. Scopes et al., J. Med. Chem., 35, 490 (1992).

Preferred examples of opioid κ receptor agonist compound still also include the compounds represented by the following Formula (IV):

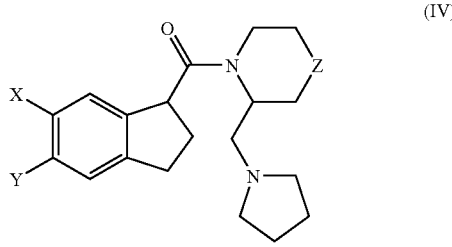

[wherein X and Y independently represent hydrogen or chlorine; and Z represents —CH$_2$—, —O— or —S—; said Formula (IV) includes (+) isomer, (−) isomer and (±) isomer] and pharmaceutically acceptable acid addition salts thereof.

Among the compounds represented by Formula (IV), 3-(1-pyrrolidinylmethyl)-4-[5,6-dichloro-1-indanecarbonyl]-tetrahydro-1,4-thiazine is preferred.

The opioid κ receptor agonist compounds represented by Formula (IV) may be produced by the method described in WO94/05646.

Preferred examples of opioid κ receptor agonist compound still also include the compounds represented by the following Formula (V):

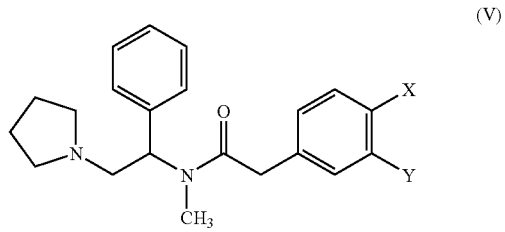

[wherein X and Y independently represent hydrogen or chlorine; said Formula (V) includes (+) isomer, (−) isomer and (±) isomer] and pharmaceutically acceptable acid addition salts thereof.

Among the compounds represented by Formula (V), 2-(3, 4-dichlorophenyl)-N-methyl-N-[1-phenyl-2-(1-pyrrolidinyl)ethyl]acetamide is preferred.

The opioid κ receptor agonist compounds represented by Formula (V) may be produced by the method described in J. J. Barlow et al., J. Med. Chem., 34, 3149 (1991).

Examples of the pharmaceutically preferred acid addition salts of the opioid κ receptor agonist compounds represented by the above-described Formulae (I) to (V) include inorganic acid salts such as hydrochloric acid salt, sulfuric acid salt, nitric acid salt, hydrobromic acid salt, hydriodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methane sulfonic acid salt, ethane sulfonic acid salt, benzene sulfonic acid salt, p-toluene sulfonic acid salt and camphor sulfonic acid salt. Among these, hydrochloric acid salt, hydrobromic acid salt, phosphoric acid salt, tartaric acid salt, methane sulfonic acid salt and the like are preferred, although, needless to say, the acid addition salts are not restricted to these salts.

These opioid κ receptor agonist compounds may be orally or parenterally administered as they are or in the form of a pharmaceutical composition after being admixed with a known pharmaceutically acceptable salt, carrier, vehicle or the like.

As oral formulations, tablets and capsules may be employed. As parenteral formulations in the form of an injection solution, percutaneous absorption preparation, tape, ointment, cream, stupe, liniment, patch, external solution, eye drop, ear drop or nasal drop may also be employed. These formulations may be prepared by the well-known methods usually employed in the field of pharmaceuticals.

The content of the opioid κ receptor agonist compound in a pharmaceutical composition is not restricted, and may usually be, for example, 0.1 μg to 100 mg in oral formulations, 0.01 μg to 10 mg in injection solutions, and 0.001 ng/m$^2$ to 100 μg/m$^2$ per one application in percutaneous or external preparations.

The administration dose may be appropriately selected depending on the symptom, age and the like of the patient, and may usually be, about 0.1 μg to 100 mg for oral administration, and about 0.01 μg to 10 mg for parenteral administration, in terms of the amount of the effective component for per day per adult.

The disorders for which the therapeutic drug is to be applied are nervous disorders, particularly, RLS, PLM, myoclonic syndrome, contraction, painful contraction and the like, especially restless legs syndrome.

EXAMPLE

Our compositions and processes will now be described more concretely by way of an example.

Example 1

A solution containing 10 μg of (−)-17-(cyclopropylmethyl)-3,14β-dihydroxy-4,5α-epoxy-6β[N-methyl-trans-3-(3-furyl)acrylamide]morphinan hydrochloric acid salt 1

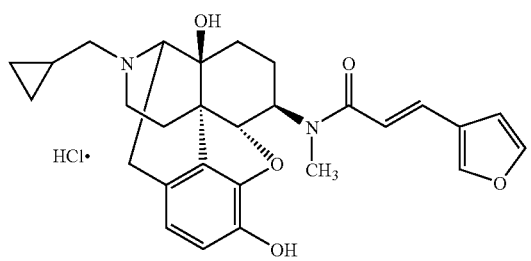

was encapsulated into a soft capsule made of gelatin to obtain an oral preparation. This oral preparation was administered to two patients who had been diagnosed as restless legs syndrome. Both of the two patients complained abnormal itchy sensation on the lower limbs and sleep is sometimes disturbed. By taking the oral preparation, the abnormal sensation disappeared 2 hours after taking the preparation in one patient, and 4 hours after taking the preparation in another patient. In both of the two patients, the effect for eliminating the abnormal sensation continued at least for 24 hours, so that sleep disturbance did not occur in the night and they could fall asleep. Thus, it was recognized that the drug clearly had therapeutic effect against restless legs syndrome.

INDUSTRIAL AVAILABILITY

The therapeutic drug for psychoneurotic disorders are useful for the therapies of nervous disorders, especially restless legs syndrome.

The invention claimed is:

1. A method of treating restless legs syndrome comprising orally or parenterally administering a therapeutically effective amount of an opioid κ receptor agonist compound represented by the following Formula (I):

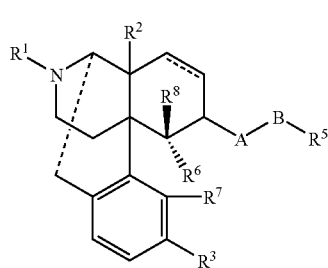

(I)

wherein ═══ represents a single bond; $R^1$ represents $C_4$-$C_7$ cycloalkylalkyl or cyclopropylmethyl; $R^2$ represents hydroxy; $R^3$ represents hydroxy; A represents —XC(═Y)— (wherein X represents $NR^4$; Y represents O; $R^4$ represents $C_1$-$C_5$ linear or branched alkyl); B represents $C_2$ linear acyclic unsaturated hydrocarbon containing 1 double bond; $R^5$ represents an organic group having the following skeleton:

(wherein Q represents —O—);
$R^6$ and $R^7$ cooperatively represent —O—; and $R^8$ hydrogen; said Formula (I) includes (+) isomer, (−) isomer and (±) isomer, or a pharmaceutically acceptable acid addition salt thereof to a patient in need thereof.

2. The method according to claim 1, wherein the pharmaceutically acceptable acid addition salt thereof is: (−)-17-(cyclopropylmethyl)-3,14β-dihydroxy-4,5α-epoxy-6β[N-methyl-trans-3-(3-furyl)acrylamido]morphian hydrochloric acid salt.

3. A method of treating restless legs syndrome and related sleep disturbance comprising orally or parenterally administering a therapeutically effective amount of an opioid κ receptor agonist compound represented by the following Formula (I):

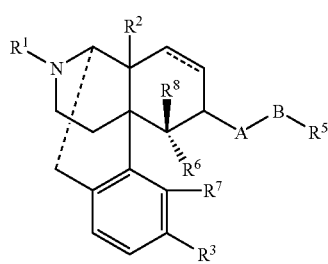

(I)

wherein ═══ represents a single bond; $R^1$ represents $C_4$-$C_7$ cycloalkylalkyl or cyclopropylmethyl; $R^2$ represents hydroxy; $R^3$ represents hydroxy; A represents —XC(═Y)— (wherein X represents $NR^4$; Y represents O; $R^4$ represents $C_1$-$C_5$ linear or branched alkyl); B represents $C_2$ linear acyclic unsaturated hydrocarbon containing 1 double bond; $R^5$ represents an organic group having the following skeleton:

(wherein Q represents —O—);
$R^6$ and $R^7$ cooperatively represent —O—; and $R^8$ represents hydrogen; said Formula (I) includes (+) isomer, (−) isomer and (±) isomer, or a pharmaceutically acceptable acid addition salt thereof to a patient in need thereof.

4. The method according to claim 3, wherein the pharmaceutically acceptable acid addition salt thereof is: (−)-17-(cyclopropylmethyl)-3,14β-dihydroxy-4,5α-epoxy-6β[N-methyl-trans-3-(3-furyl)acrylamido]morphian hydrochloric acid salt.

5. A method of treating sleep disturbance caused by restless legs syndrome comprising orally or parenterally administering a therapeutically effective amount of an opioid κ receptor agonist compound is represented by the following Formula (I):

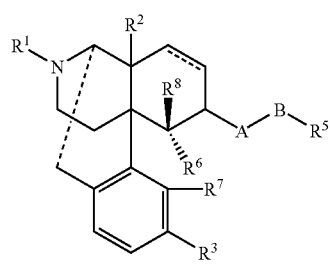

(I)

wherein ═══ represents a single bond; $R^1$ represents $C_4$-$C_7$ cycloalkylalkyl or cyclopropylmethyl; $R^2$ represents hydroxy; $R^3$ represents hydroxy; A represents —XC(═Y)— (wherein X represents $NR^4$; Y represents O; $R^4$ represents $C_1$-$C_5$ linear or branched alkyl); B represents $C_2$ linear acyclic unsaturated hydrocarbon containing 1 double bond; $R^5$ represents an organic group having the following skeleton:

(wherein Q represents —O—);

$R^6$ and $R^7$ cooperatively represent —O—; and $R^8$ hydrogen; said Formula (I) includes (+) isomer, (−) isomer and (±) isomer, or a pharmaceutically acceptable acid addition salt thereof to a patient in need thereof.

6. The method according to claim 5, wherein the pharmaceutically acceptable acid addition salt thereof is: (−)-17-(cyclopropylmethyl)-3,14β-dihydroxy-4,5α-epoxy-6β[N-methyl-trans-3-(3-furyl)acrylamido]morphian hydrochloric acid salt.

* * * * *